ns Patent [19]

United States Patent [19]

Condon et al.

[11] Patent Number: 5,252,536
[45] Date of Patent: Oct. 12, 1993

[54] SUBSTITUTED INDOLINONES USEFUL AS HERBICIDAL AGENTS

[75] Inventors: Michael E. Condon, Lawrenceville; Gary M. Karp, Princeton Junction, both of N.J.

[73] Assignee: American Cyanamid Company, Stamford, Conn.

[21] Appl. No.: 815,674

[22] Filed: Dec. 31, 1991

[51] Int. Cl.$^5$ .................. A01N 43/36; C07D 209/34
[52] U.S. Cl. .................................. 504/100; 504/284; 548/411; 548/460; 548/461
[58] Field of Search ............ 548/460, 411, 461; 71/95, 77, 284; 504/100

[56] References Cited

FOREIGN PATENT DOCUMENTS 0332009 9/1989 European Pat. Off. ............ 548/411

OTHER PUBLICATIONS

CA 111(19):174127x Preparation of . . . as herbicides, Ganzer et al. p. 728, 1989.

*Primary Examiner*—Mary C. Lee
*Assistant Examiner*—Joseph K. McKane
*Attorney, Agent, or Firm*—Michael P. Morris

[57] ABSTRACT

Substituted indolinone compounds which are effective in the control of undesirable plant species are described. Also described are a method for the herbicidal use of the compounds and a method for their preparation.

20 Claims, No Drawings

SUBSTITUTED INDOLINONES USEFUL AS HERBICIDAL AGENTS

BACKGROUND OF THE INVENTION

Certain N-Aryltetrahydrophthalimide derivatives are described as herbicides in European Patent application 332,009 published Sep. 13, 1989. It has now been found that substituted indolinones demonstrate selectivity towards agronomic crops while providing excellent control of a wide variety of undesirable plant species.

SUMMARY OF THE INVENTION

The present invention describes substituted indolinone compounds which are useful as herbicidal agents.

The substituted indolinone compounds of the present invention are illustrated as structural formula I:

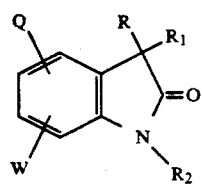

wherein
R and $R_1$ are each independently hydrogen,
  $C_1$–$C_6$ alkyl optionally substituted with hydroxy, $C_1$–$C_4$ alkoxy, mercapto, $C_1$–$C_4$ alkylthio, amino, carboxy or carb($C_1$–$C_4$)alkyloxy,
  $C_3$–$C_6$ cycloalkyl optionally substituted with $C_1$–$C_6$ alkyl, hydroxy, $C_1$–$C_4$ alkoxy, mercapto, $C_1$–$C_4$ alkylthio, amino, carboxy or carb($C_1$–$C_4$)alkyloxy,
  $C_1$–$C_6$ alkoxy,
  $C_1$–$C_6$ alkylthio,
  $C_3$–$C_6$ alkenyl, or
  $C_3$–$C_6$ alkynyl; and when R and $R_1$ are taken together with the carbon to which they are attached they represent saturated or unsaturated $C_3$–$C_7$ cycloalkyl optionally interrupted by O, S, or N;
$R_2$ is hydrogen,
  $C_1$–$C_4$ alkyl optionally substituted with $C_1$–$C_4$ alkoxy, $C_1$–$C_4$ alkylthio, carboxy or carb($C_1$–$C_4$)alkyloxy,
  $C_3$–$C_4$ cycloalkyl optionally substituted with $C_1$–$C_4$ alkoxy, $C_1$–$C_4$ alkylthio, carboxy or carb($C_1$–$C_4$) alkyloxy,
  $C_3$–$C_4$ alkenyl,
  $C_3$–$C_4$ alkynyl, or cyclopropylmethyl;
W is hydrogen, halogen,
  $C_1$–$C_3$ alkoxy optionally substituted with one or more halogen atoms, or
  $C_1$–$C_3$ alkyl optionally substituted with one or more halogen atoms;
Q is selected from

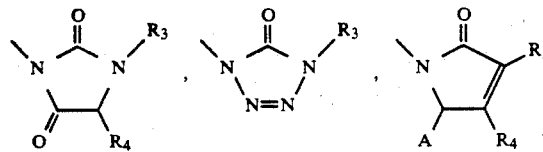

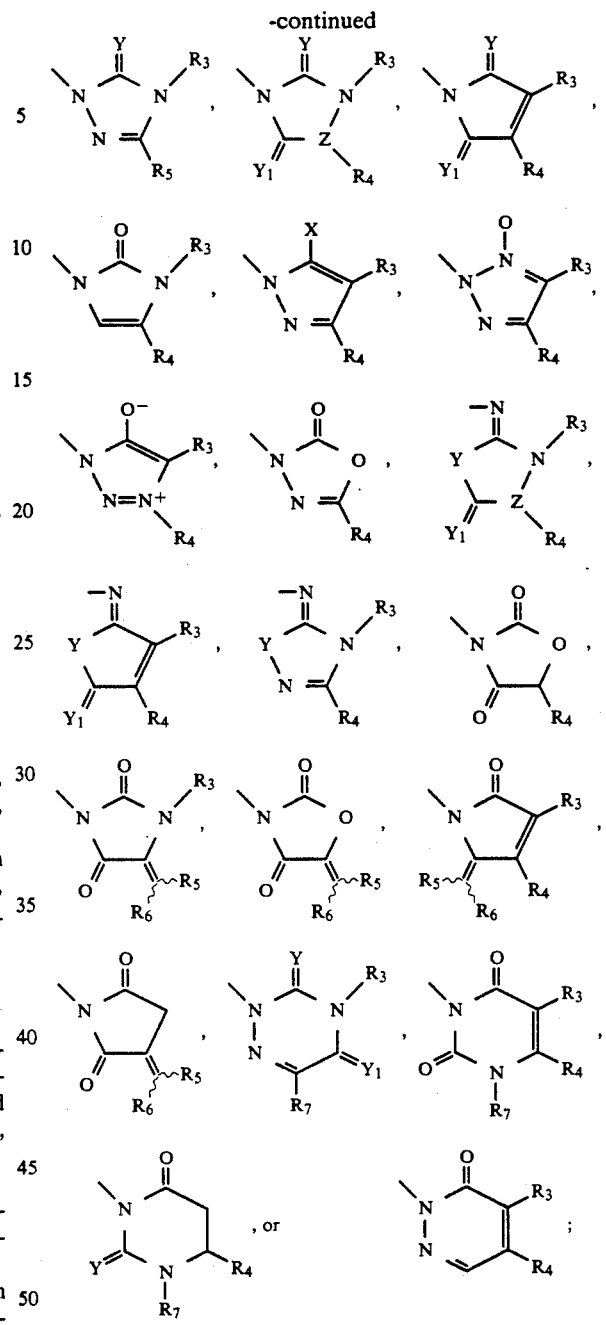

$R_3$ and $R_4$ are each independently
  $C_1$–$C_6$ alkyl optionally substituted with one or more halogen atoms, or
  $C_3$–$C_6$ cycloalkyl optionally substituted with one or more halogen atoms; and
  when $R_3$ and $R_4$ are taken together with the atoms to which they are attached they represent a four- to seven-membered saturated or unsaturated ring optionally interrupted by O, S, or N, and optionally substituted with one to three methyl groups or one or more halogen atoms;
$R_5$, $R_6$ and $R_7$ are each independently hydrogen or $C_1$–$C_3$ alkyl;
X is halogen or $C_1$–$C_3$ alkyl;
Y and $Y_1$ are each independently O or S;
Z is N or CH; and A is hydroxy, halogen, $C_1-C_3$ alkoxy or $C_1-C_3$ alkylthio;

with the proviso that when W is on the five position of the indolinone ring and Q is

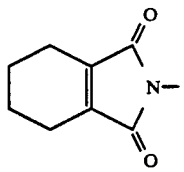

and is on the six position of the indolinone ring, then at least one of R and $R_1$ is a substituent other than hydrogen.

The compounds of the present invention demonstrate selectivity on important agronomic crops such as corn, soybeans, rice and wheat while effectively controlling numerous weed species.

DETAILED DESCRIPTION OF THE INVENTION

A preferred group of substituted indolinone compounds that is especially useful for the control of undesirable plant species is illustrated by formula II

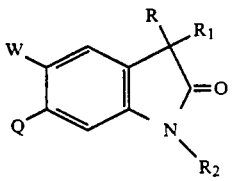

wherein R, $R_1$, $R_2$, W and Q are as described above for formula I.

More preferred formula II compounds of the invention which are especially useful for the control of undesirable plant species in agronomic crops are illustrated as structural formula III

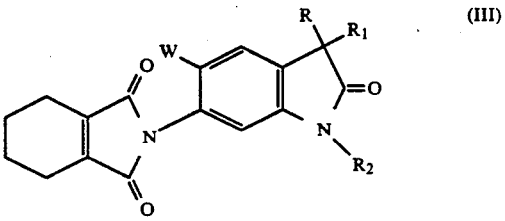

wherein
R is hydrogen or $C_1-C_6$ alkyl;
$R_1$ is $C_1-C_6$ alkyl or $C_1-C_6$ alkylthio; and when R and $R_1$ are taken together with the carbon to which they are attached they represent $C_3-C_7$ cycloalkyl;
$R_2$ is $C_1-C_4$ alkyl optionally substituted with $C_1-C_4$ alkoxy or $C_1-C_4$ alkylthio,
$C_3-C_4$ cycloalkyl,
$C_3-C_4$ alkenyl,
$C_3-C_4$ alkynyl, or cyclopropylmethyl; and
W is hydrogen or halogen.

In formulas I–III above, the term halogen designates F, Cl, Br or I.

Surprisingly, the substituted indolinone compounds of the present invention demonstrate selectivity on important agronomic crops such as corn, soybeans, rice and wheat while effectively controlling numerous undesirable plant species.

Certain formula I substituted indolinone compounds are prepared as shown in Flow Diagram I:

FLOW DIAGRAM I

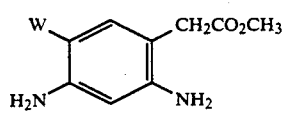

↓ HCl/H₂O

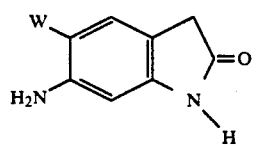

↓

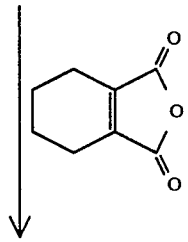

↓

-continued
FLOW DIAGRAM I
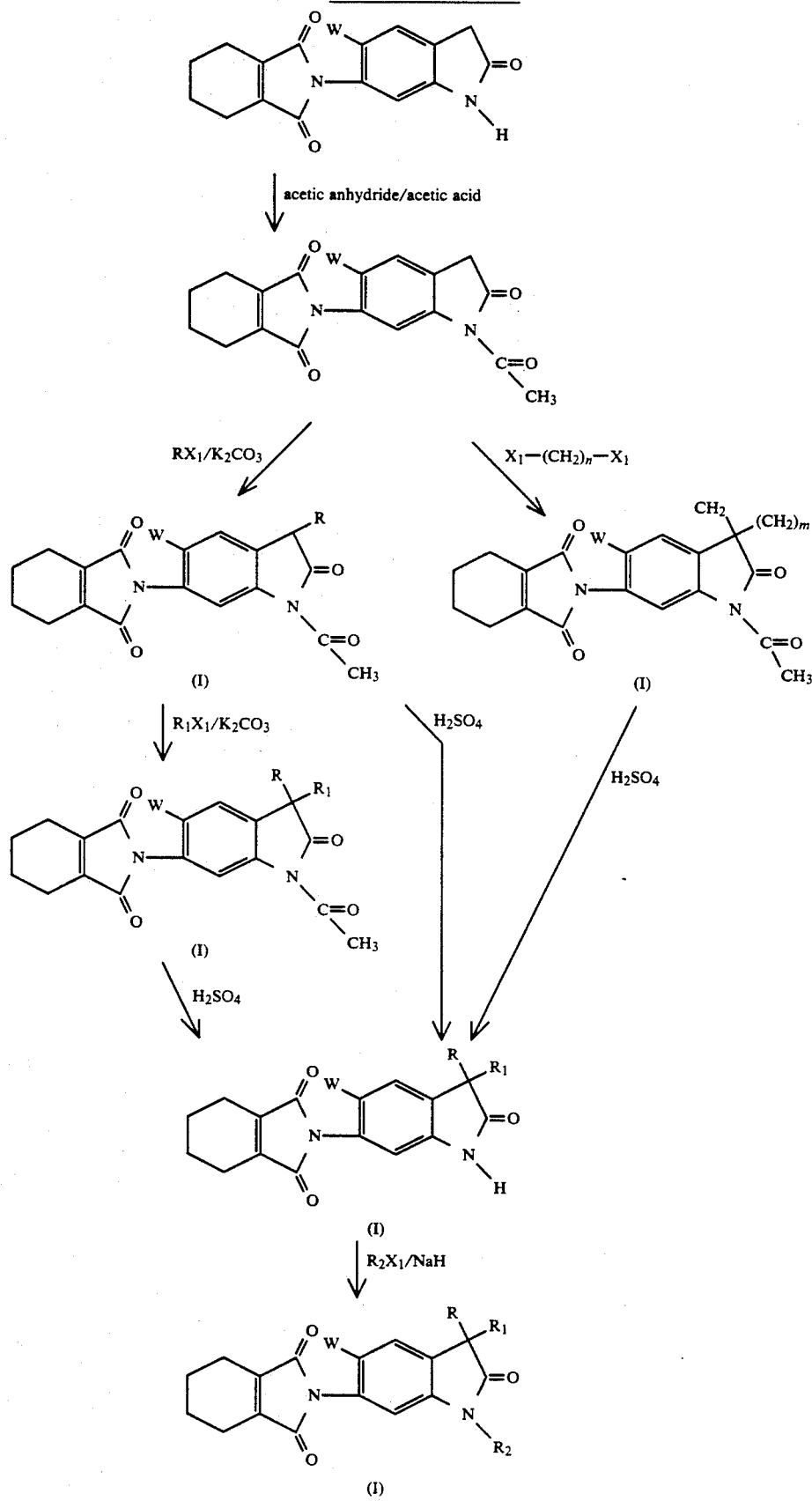

wherein $X_1$ is Cl or Br; n is an integer having a value of 2 through 6; m is an integer having a value of $n-1$; and R, $R_1$, $R_2$ and W are as described above for formula I.

Compounds of formula I may also be prepared as shown in Flow Diagram II:

useful for the control of a vide variety of undesirable plant species. These compounds are effective for controlling weeds native to both dry land and wet land areas. The compounds are also useful as aquatic herbicides and are effective in controlling the above-said

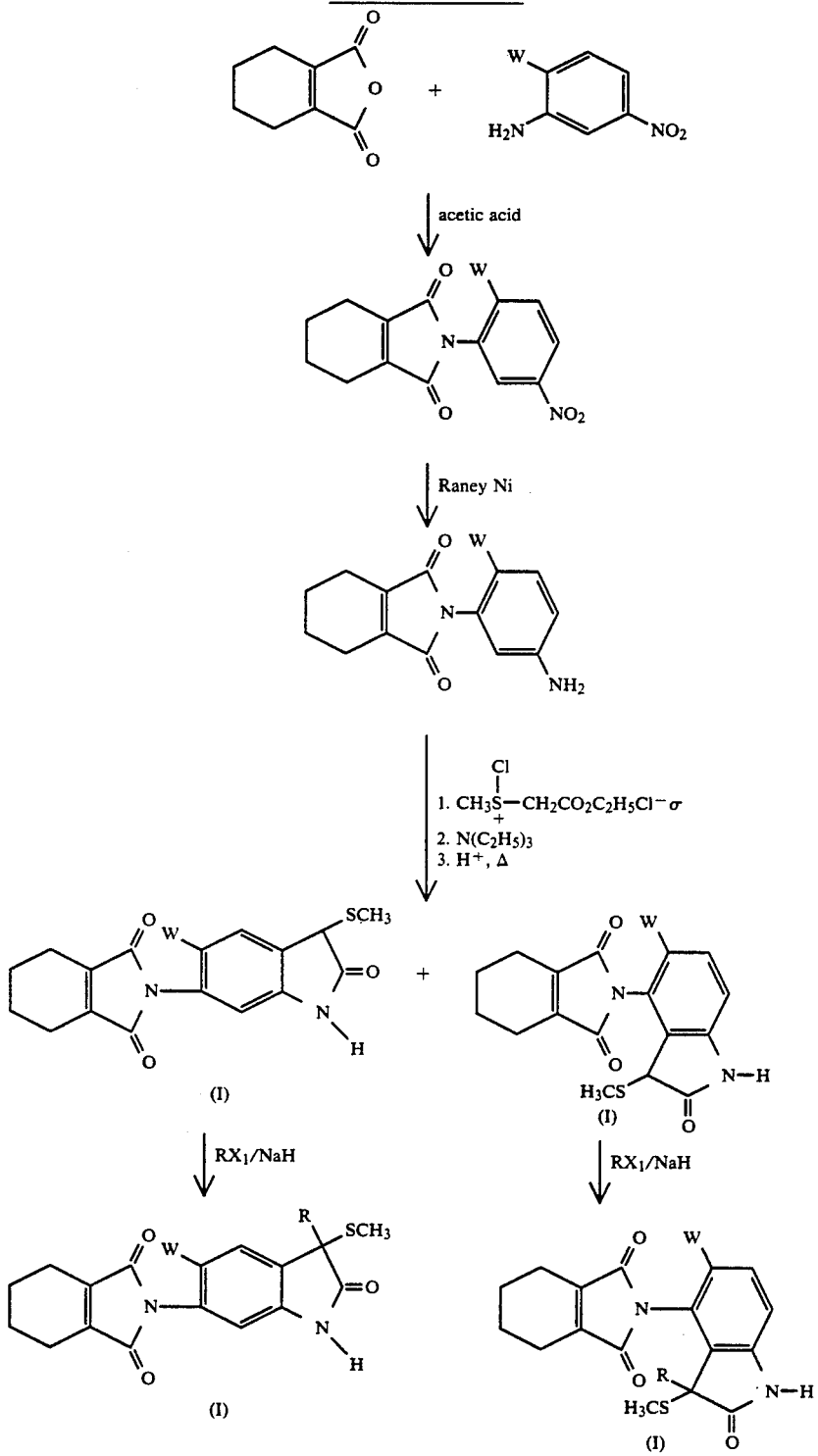

FLOW DIAGRAM II wherein $X_1$ is Cl, Br or I; W and R are as described above for formula I.

The formula I substituted indolinone compounds of the present invention are effective herbicidal agents plants when applied to the foliage thereof or to soil or water containing seeds or other propagating organs of said plants such as stolons, tubers or rhizomes, at rates of from about 0.016 to 4.0 kg/ha and preferably from about 0.125 to 4.0 kg/ha.

The compounds of the invention are effective for controlling undesirable plant species including important weeds in transplanted rice culture. The compounds may be applied to the soil or water containing transplanted rice plants and seeds or other propagating organs of a variety of weed species.

The formula I substituted indolinone compounds can be formulated as emulsifiable concentrates, wettable powders, granular formulations, flow concentrates and the like.

In order to facilitate a further understanding of the invention, the following examples are presented to illustrate more specific details thereof. The invention is not to be limited thereby except as defined in the claims. The term NMR designates nuclear magnetic resonance spectroscopy.

EXAMPLE I

Preparation of Methyl (5-fluoro-2,4-dinitrophenyl)acetate

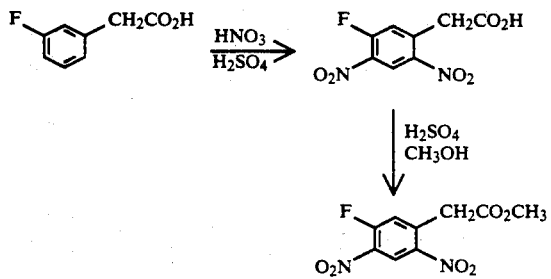

A solution of nitric acid (90%, 24 mL) and concentrated sulfuric acid (30 mL) is added dropwise over 1 hour to a solution of m-fluorophenylacetic acid (20.0 g, 130 mmol) and concentrated sulfuric acid (40 mL) while maintaining the reaction temperature between 20°-35° C. The reaction mixture is stirred overnight at 35° C., poured onto ice, filtered and washed with water to give a white solid which is dried in a vacuum oven at 75° C. for 5 hours. A solution of the thus-formed solid (29.5 g), concentrated sulfuric acid (1 mL) and methanol is heated at reflux for 5 hours and cooled to room temperature overnight. The reaction mixture is cooled in an ice-bath and the pH is brought to a value of about 5 with 3N sodium hydroxide solution. The solvent is removed in vacuo to give a solution which is partitioned between ethyl acetate and water. The organic phase is separated, washed sequentially with water and sodium chloride, dried and concentrated in vacuo to give a light brown oil. Chromatography of the oil using silica gel and 15-20% ethyl acetate/hexanes gives the title product as an amber oil (16.3 g) which is identified by $^1$H and $^{13}$C NMR spectral analyses.

EXAMPLE 2

Preparation of 6-Amino-5-fluoro-2-indolinone

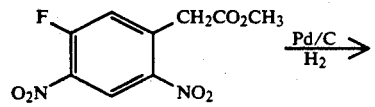

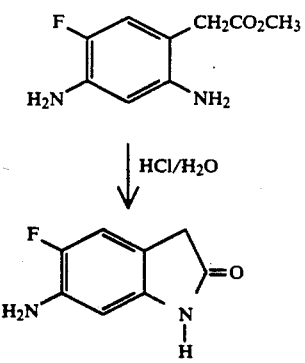

A mixture of 10% Pd on carbon (2.44 g, 10% by weight), methyl (5-fluoro-2,4-dinitrophenyl)acetate (24.4 g, 93.8 mmol), ethylene glycol dimethyl ether (100 mL) and ethanol (100 mL) is hydrogenated on a Parr hydrogenator for 1½ hours. After the uptake of 47-48 psi, the reaction mixture is removed from the hydrogenator. The catalyst is filtered and the filtrate is concentrated in vacuo to give a dark oil. The oil is diluted with 1M hydrochloric acid, heated at reflux for 20 minutes, cooled to room temperature and the pH is adjusted to 8 with 3N sodium hydroxide solution. The pH adjusted solution is extracted with ethyl acetate and the combined organic extracts are dried and concentrated in vacuo to give the title product as a light brown solid (13.2 g, mp 185°-187° C. dec) which is identified by $^1$H NMR spectral analysis.

Following the procedure of Example 2, but substituting ethyl (2,4-dinitrophenyl)acetate for methyl (5-fluoro-2,4-dinitrophenyl)acetate gives 6-amino-2-indolinone as a tan solid, mp 194°-195 C.

EXAMPLE 3

Preparation of N-(5-Fluoro-2-oxo-6-indolinyl)-1-cyclohexene-1,2-dicarboximide

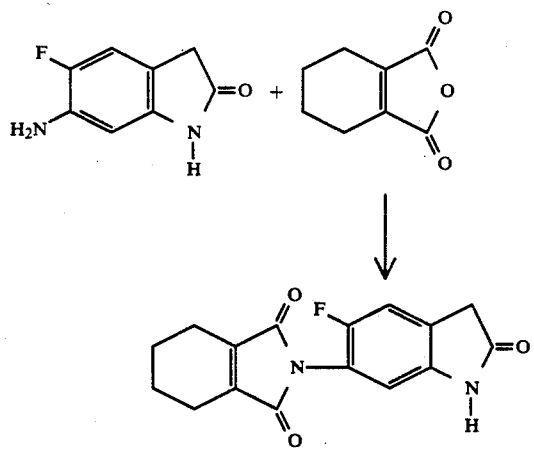

A mixture of 6-amino-5-fluoro-2-indolinone (10.5 g, 63.25 mmol) and tetrahydrophthalic anhydride (10.95 g, 66.42 mmol) in acetic acid (30 mL) is heated at reflux for 2 hours, cooled and concentrated in vacuo to obtain a residue. Chromatography of the residue using silica gel and a 3:7 ethyl acetate/methylene chloride solution gives the title product as a light violet solid (14.7 g, mp 234°–236° C.). Following the procedure of Example 3, but substituting 6-amino-2-indolinone for 6-amino-5-fluoro-2-indolinone gives N-(2-oxo-6-indolinyl)-1-cyclohexene-1,2-dicarboximide as a green solid, mp 225°–226° C.

EXAMPLE 4

Preparation of
N-(1-Acetyl-5-fluoro-2-oxo-6-indolinyl)-1-cyclohexene-1,2-dicarboximide

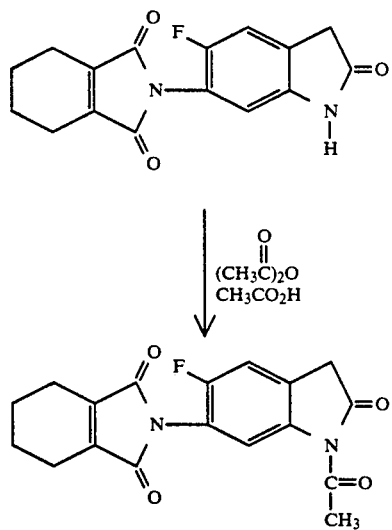

A solution of N-(S-fluoro-2-oxo-6-indolinyl)-1-cyclohexene-1,2-dicarboximide (14.7 g, 49 mmol), acetic anhydride (7 mL, 73.5 mmol) and acetic acid (12 mL) is heated at reflux for 6 hours, treated with additional acetic anhydride (2.4 mL), heated at reflux for 1½ hours, treated with additional acetic anhydride (2.4 mL), heated at reflux for 17.5 hours, cooled and concentrated in vacuo to give a brown semi-solid. The semi-solid is stirred in 20% ethyl acetate/hexanes and filtered to obtain the title product as a light brown solid (15.32 g, mp 191°–193.5° C.).

Following the procedure of Example 4, but substituting N-(2-oxo-6-indolinyl)-1-cyclohexene-1,2-dicarboximide for N-(5-fluoro-2-oxo-6-indolinyl)-1-cyclohexene-1,2-dicarboximide yields N-(1-acetyl- 2-oxo-6-indolinyl)-i-cyclohexene-1,2-dicarboximide as pale tan crystals, mp 214°–215° C.

EXAMPLE 5

Preparation of
N-1'-Acetyl-5'-fluoro-2'-oxospiro-[cyclopropane-1,3'-indolin]-6'-yl)-1-cyclohexene-1,2-dicarboximide

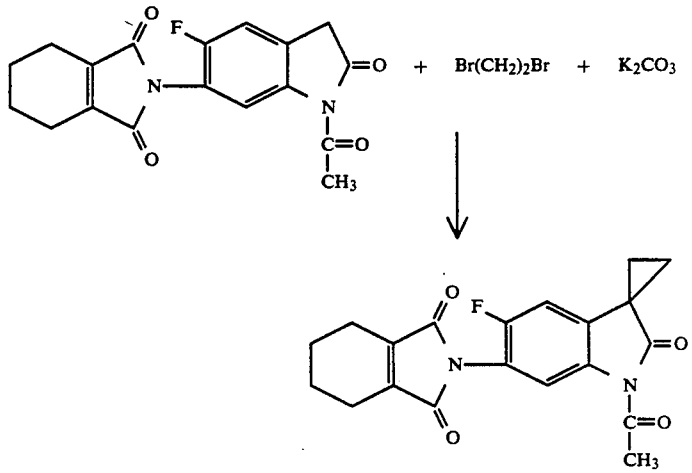

1,2-Dibromoethane (2.81 g, 14.96 mmol) and potassium carbonate (1.88 g, 13.6 mmol) are added to a solution of N-(1-acetyl-5-fluoro-2-oxo-6-indolinyl)-1-cyclohexene-1,2-dicarboximide (4.65 g, 13.6 mmol) in dimethyl sulfoxide (50 mL). The reaction mixture is stirred for 2 hours, treated with additional potassium carbonate (0.94 g), stirred for 2½ hours, treated with additional potassium carbonate (0.94 g), stirred for 18.5 hours, poured into water and partitioned with ether. The organic phase is washed sequentially with water and brine, dried and concentrated in vacuo to obtain a residue. Chromatography of the residue using silica gel and a 15%–20% ethyl acetate/hexane solution gives the title compound as a tan solid (1.04 g, mp 199°–201° C.)

Following the procedure of Example 5, but substituting N-(1-acetyl-2-oxo-6-indolinyl)-1-cyclo-hexene-1,2-dicarboximide for N-(1-acetyl-5-fluoro-2-oxo-6-indolinyl)-1-cyclohexene-1,2-dicarboximide yields N-(1'-acetyl-2'-oxospiro[cyclopropane-1,3'-indolin]-6'-yl)-1-cyclohexene-1,2-dicarboximide as yellow crystals, mp 237°–238° C.

EXAMPLE 6

Preparation of
N-{5'-Fluoro-2'-oxospiro[cyclopropane-1,3'-indolin]-6,-yl}-1-cyclohexene-1,2-dicarboximide

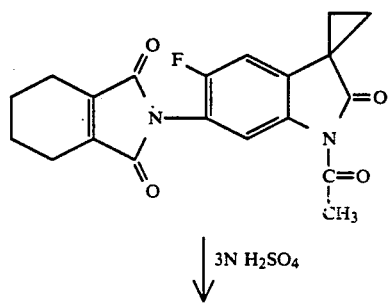

-continued

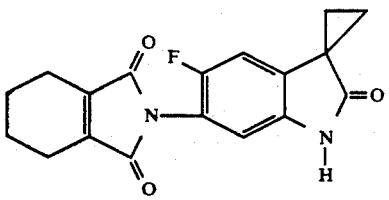

A solution of N-(1'-acetyl-5'-fluoro-2'-oxospiro[cyclopropane-1,3'-indolin]-6'-yl)-1-cyclohexene-1,2-dicarboximide (3.05 g, 8.29 mmol), sulfuric acid (3 N, 30 mL) and tetrahydrofuran (30 mL) is heated at reflux for 3 hours, cooled and partitioned with ethyl acetate. The organic phase is washed sequentially with water and saturated sodium hydrogen carbonate solution, dried and concentrated in vacuo to give the title product as a tan solid (1.92 g, mp 284°–285° C.).

Following the procedure of Example 6, but substituting N-(1'-acetyl-2'-oxospiro[cyclopropane-1,3'-indolin]-6'-yl)-1-cyclohexene-1,2-dicarboximide for N-(1'-acetyl-5'-fluoro-2'-oxospiro[cyclopropane-1,3'-indolin]-6'-yl)-cyclohexene-1,2-dicarboximide yields N-(2'-oxospiro[cyclopropane-1,3'-indolin]-6'-yl)1-cyclohexene-1,2-dicarboximide as tan crystals, mp 274.5°–276° C.

EXAMPLE 7

Preparation of 6'-(1-Cyclohexene-1,2-dicarboximido)-5'-fluoro-1'-(2-propynyl)spiro[cyclolpropane-1,3'-indolin]-2,-one

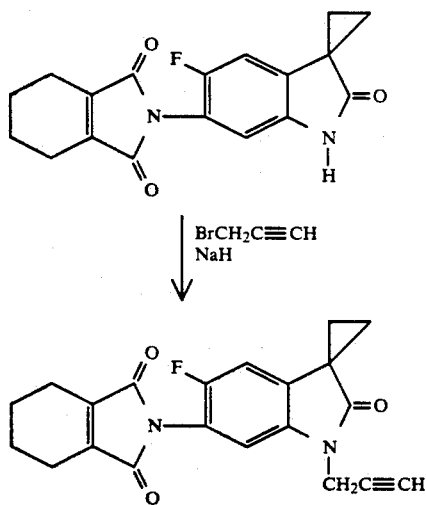

A solution of N-(5'-fluoro-2'-oxospiro[cyclopropane-1,3'-indolin]-6'-yl)-1-cyclohexene-1,2-dicarboximide (0.6 g, 1.84 mmol) in dimethylformamide (5 mL) is added over 5 minutes to a mixture of sodium hydride (0.08 g, 2.02 mmol) in dimethylformamide (5 mL) at −10° C. The reaction mixture is stirred for 20 minutes at −10° C., then a solution of propargyl bromide (0.26 g, 2.21 mmol) in dimethylformamide (5 mL) is added. The reaction mixture is stirred for 2 hours at −10° C., 2½ hours at 10° C., 4 hours at 20° C. and 15½ hours at 35° C. The reaction mixture is cooled to 0° C. and additional sodium hydride (0.05 g) is added. The reaction mixture immediately turns dark and is poured into an ether/water mixture. The organic phase is separated, washed sequentially with water and brine, dried and concentrated in vacuo to obtain a brown residue. Chromatography of residue using silica gel and a 25% ethyl acetate/hexanes solution gives the title product as a white solid (0.13 g, mp 209°–212° C.) which is identified by $^1$H and $^{13}$C NMR spectral analyses.

Following the above procedure, but using N-{2,oxospiro[cyclopropane-1,3'-indolin]-6'-yl}-1-cyclohexene-1,2-dicarboximide or N-{5'-fluoro-2'-oxospiro[cyclopropane-1,3'-indolin]-6'-yl)-1-cyclohexene-1,2-dicarboximide and the appropriate alkylating agent yields the compounds shown below.

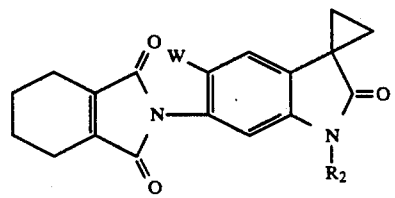

| W | $R_2$ | mp °C. |
|---|---|---|
| F | —CH$_3$ | 251–252 |
| H | —CH$_3$ | 231–232 |
| H | —CH$_2$—C≡CH | 201–203 |
| H | —CH$_2$CH=CH$_2$ | 167–169 |
| H | —CH$_2$OCH$_3$ | 162–163 |

EXAMPLE 8

Preparation of N-(2-Fluoro-5-nitrophenyl)-1-cyclohexene-1,2-dicarboximide

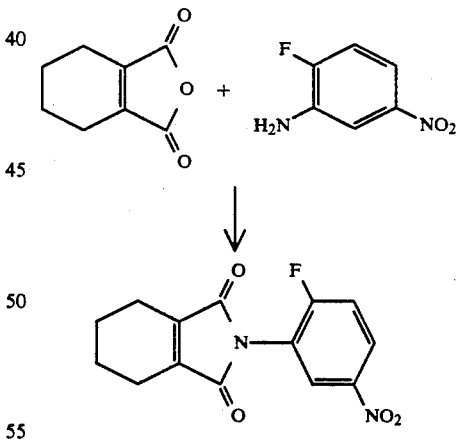

A mixture of 3,4,5,6-tetrahydrophthalic anhydride (22.8 g, 150 mmol), 2-fluoro-5-nitroaniline (23.4 g, 150 mmol) in glacial acetic acid is heated at reflux for 23 hours, cooled and poured into a water/toluene mixture. The organic phase is separated, washed sequentially with water and saturated sodium hydrogen carbonate solution, dried and concentrated in vacuo to obtain a yellow solid. Recrystallization of the solid from ethanol gives the title compound as off-white plates (26.6 g, mp 154°–156° C.) which are identified by $^1$H and $^{13}$C NMR spectral analyses.

EXAMPLE 9

Preparation of
N-(5-Amino-2-fluorophenyl)-1-cyclohexene-1,2-dicarboximide

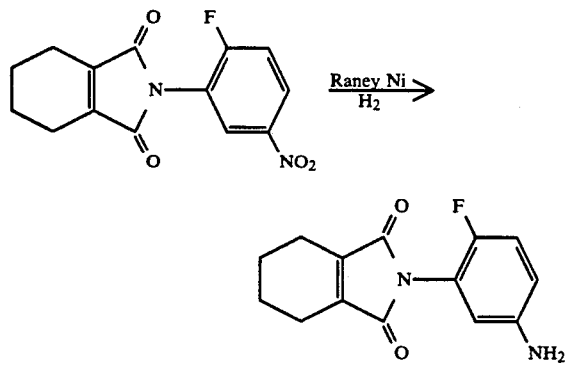

Wet Raney Nickel (0.9 g) is added to a solution of N-(2-fluoro-5-nitrophenyl)-1-cyclohexene-1,2-dicarboximide (1.0 g, 3.4 mmol) in a 4:1 ethylene glycol dimethyl ether/ethanol solution. The reaction mixture is hydrogenated over 45 psi of hydrogen until the reaction mixture takes up 9 psi. The reaction mixture is filtered through diatomaceous earth and concentrated in vacuo to obtain a yellow residue. Chromatography of the residue gives the title product as a yellow-orange solid (0.84 g, mp 134°-136° C.) which is identified by $^1$H and $^{13}$C NMR spectral analyses.

EXAMPLE 10

Preparation of
N-[5-Fluoro-3-(methylthio)-2-oxo-6-indolinyl]-1-cyclohexene-1,2-dicarboximide and
N-[5-fluoro-3-(methylthio)-2-oxo-4-indolinyl]-1-cyclohexene-1,2-dicarboxiiaide

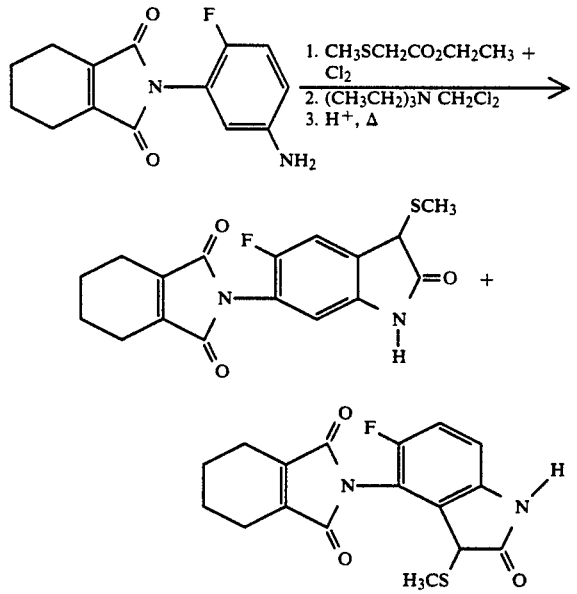

A solution of ethyl methylthioacetate (28.5 mL, 220 mmol) in methylene chloride is added to a solution of chlorine gas (10.5 mL, 230 mmol) in methylene chloride at −78 C. After stirring for 5 minutes, a solution of N-(5-amino-2-fluorophenyl)-1-cyclohexene-1,2-dicarboximide (52.0 g, 200 mmol), triethylamine (27.8 mL, 200 mmol) in methylene chloride is added to the reaction mixture over 1 hour. The reaction mixture is stirred for 1 hour at −78° C. and additional triethylamine (41.5 mL, 300 mmol) is added. The reaction mixture is warmed to room temperature with stirring over 1½ hours then poured into water. The organic phase is separated, dried and concentrated in vacuo to obtain a dark brown oil. Toluene and p-toluenesulfonic acid (1.9 g) are added to the oil and the mixture is heated at reflux for 4 hours, cooled to room temperature and filtered to obtain a solid. Recrystallization of the solid from a methylene chloride/hexane solution gives N-[5-fluoro-3-(methylthio)-2-oxo-4-indolinyl]-i-cyclohexene-1,2-dicarboximide as a white solid (mp 225°-226° C.) and from the mother liquor N-[5-fluoro-3-(methylthio)-2-oxo-6-indolinyl]-1-cyclohexene-1,2-dicarboximide crystallizes as a tan solid (mp 252°-255° C. dec).

EXAMPLE 11

Preparation of
N-[5-Fluoro-3-methyl-3-methylthio)-2-oxo-6-indolinyl]-1-cyclohexene-1,2-dicarboximide

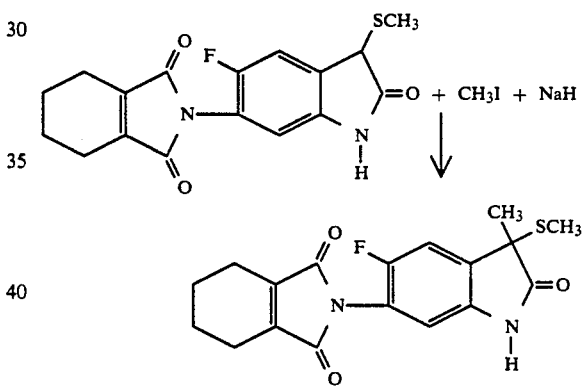

A mixture of N-[5-fluoro-3-(methylthio)-2-oxo-6-indolinyl]-1-cyclohexene-1,2-dicarboximide (6.0 g, 17.34 mmol) and sodium hydride (0.73 g, 18.21 mmol) in dimethyl sulfoxide is stirred for 30 minutes. A solution of methyl iodide in dimethyl sulfoxide is then added dropwise and the reaction mixture is stirred for 2 hours and poured into an ether/water mixture. Ethyl acetate is added and the organic phase is separated, washed sequentially with water and brine, dried and concentrated in vacuo to obtain a solid. The solid is triturated in an ethyl acetate/hexane solution and after filtration gives the title product as a tan solid (4.1 g, mp 268°-272° C. dec.) which is identified by $^1$H and $^{13}$C NMR spectral analyses.

Following the above procedure, but substituting N-[5-fluoro-3-(methylthio)-2-oxo-4-indolinyl]-1-cyclohexene-1,2-dicarboximide for N-[5-fluoro-3-(methylthio)-2-oxo-6-indolinyl]-1-cyclohexene-1,2-dicarboximide gives N-[5-fluoro-3-methyl-3-(methylthio)-2-oxo-4-indolinyl]-i-cyclohexene-1,2-dicarboximide as a yellow solid, mp 267°-271° C. (dec).

EXAMPLE 12
Preparation of
N-[5-Fluoro-1,3-dimethyl-3-(methylthio)-2-oxo-4-indolinyl]-1-cyclohexene-2,2-dicarboximide

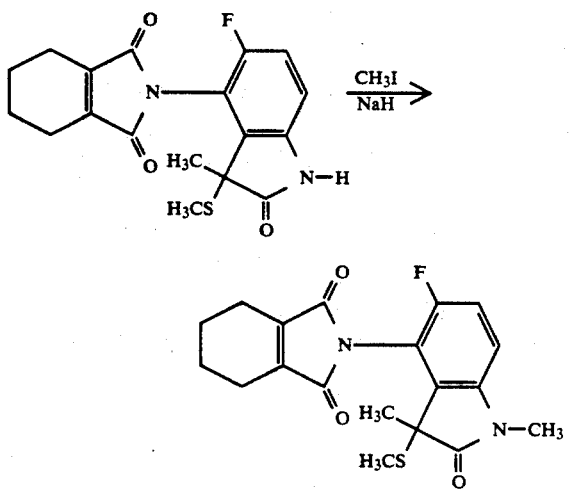

A mixture of N-[5-fluoro-3-methyl-3-(methylthio)-2-oxo-4-indolinyl]-i-cyclohexene-1,2-dicarboximide (1.32 g, 5.06 mmol) and sodium hydride (0.22 g, 5.57 mmol) in dimethyl sulfoxide is stirred for 30 minutes, treated with a solution of methyl iodide in dimethyl sulfoxide, stirred for 4 hours and poured into an ethyl acetate/water mixture. The organic phase is separated, dried and concentrated in vacuo to obtain a yellow residue. chromatography of the residue using silica gel and a 1:3 to 1:2 ethyl acetate/hexane solution gives the title product as a white solid (0.75 g, mp 2260°-228° C.) which is identified by $^1H$ and $^{13}C$ NMR spectral analyses.

EXAMPLE 13
Preparation of Ethyl (2,4-dinitrophenyl)acetate

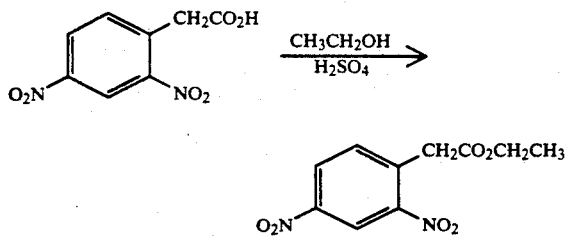

A mixture containing 2,4-dinitrophenylacetic acid (100 g, 0.442 mol), concentrated sulfuric acid (1.5 mL) and ethanol (700 mL) is heated at reflux for 6½ hours, cooled to room temperature and filtered. The filtrate is concentrated in vacuo to a volume of 200 mL then diluted with water. The pH of the aqueous mixture is adjusted to about a with solid sodium hydrogen carbonate and extracted with ether. The combined organic extracts are washed with water, dried over anhydrous sodium sulfate, decolorized with charcoal and concentrated in vacuo to obtain the title compound as a yellow oil (102.4 g).

EXAMPLE 14
Postemergence herbicidal evaluation of test compounds

The postemergence herbicidal activity of the compounds of the invention is demonstrated by the following tests wherein a variety of monocotyledonous and dicotyledonous plants are treated with test compounds dispersed in aqueous acetone mixtures. In the tests, seedling plants are grown in jiffy flats for about 2 weeks. The test compounds are dispersed in 50/50 acetone/water mixtures containing about 0.5% TWEEN, 20, a polyoxyethylene sorbitan monolaurate surfactant of Atlas Chemical Industries, in sufficient quantity to provide the equivalent of about 0.032 to 4.0 kg per hectare of active compound when applied to the plants through a spray nozzle operating at 40 psi for a predetermined time. After spraying, the plants are placed on greenhouse benches and are cared for in the manner commensurate with conventional greenhouse practices. From 1 to 2 weeks after treatment, the seedling plants are examined and rated according to the rating system provided below. The data obtained are shown in Table I.

The rating scale is based upon a visual observation of plant stand, vigor, malformation, size, chlorosis and overall plant appearance as compared with a control.

| Rating | | % Control (Compared to Check) |
|---|---|---|
| 9 | Complete kill | 100 |
| 8 | Approaching Complete kill | 91-99 |
| 7 | Good Herbicidal Effect | 80-90 |
| 6 | Herbicidal Effect | 65-79 |
| 5 | Definite Injury | 45-64 |
| 4 | Injury | 30-44 |
| 3 | Moderate Effect | 16-29 |
| 2 | Slight Effect | 6-15 |
| 1 | Trace Effect | 1-5 |
| 0 | No Effect | 0 |

| Plant Species Used | | |
|---|---|---|
| Column Heading | Common Name | Scientific Name |
| Barnyard Gr | Barnyardgrass | ECHINOCHLOA CRUS-GALLI, (L) BEAU |
| Large Crab | Crabgrass, (hairy) Large | DIGITARIA SANGUINALIS, (L) SCOP |
| Green Fox | Foxtail, Green | SETARIA VIRIDIS, (L) BEAUV |
| Mrnglry Sp | Morningglory Spp. | IPOMOEA SPP. |
| Pigweed Sp | Pigweed Spp. | AMARANTHUS SPP. |
| Ragweed | Ragweed, Common | AMBROSIA ARTEMISIIFOLIA, L. |
| Velvetleaf | Velvetleaf | ABUTILON THEOPHRASTI, MEDIC. |
| Corn Field | Corn, Field | ZEA MAYS, L. |
| Soybean | Soybean | GLYCINE MAX, (L) MERR. |
| Rice Uplnd | Rice Upland | ORYZA SATIVA, L. |
| W Wheat XX | Wheat, Winter, XX | TRITICUM AESTIVUM, L |

TABLE I

Postemergence Herbicidal Evaluation of Test Compounds

| Compound | Rate kg/ha | Barnyard Gr | large crab | Green Fox | Mrngry Sp | Pigweed Sp | Rag weed | Velvet leaf | Corn Field | Soy bean | Rice Uplnd | W.Wheat at XX |
|---|---|---|---|---|---|---|---|---|---|---|---|---|
| N-[5-Fluoro-3-(methyl-thio)-2-oxo-6-indolinyl]-1-cyclohexene-1,2-dicarboximide | 0.500 0.125 | 2.0 0.5 | 1.5 2.0 | 2.0 1.5 | 5.0 4.0 | 4.5 4.5 | 4.5 4.0 | 5.0 3.0 | 2.5 1.5 | 3.0 3.0 | 0.0 0.0 | 1.0 1.0 |
| N-[(5-Fluoro-3-methyl-3-(methylthio)-2-oxo-6-indolinyl]-1-cyclohexene-1,2-dicarboximide | 0.500 0.250 | 4.0 3.0 | 4.0 3.5 | 3.5 2.0 | 7.0 8.5 | 8.0 8.0 | 7.0 6.0 | 7.5 7.5 | 3.5 2.5 | 4.0 5.0 | 0.0 0.0 | 0.0 0.0 |
| N-[5'-Fluoro-2'-oxo-spiro[cycloproane-1,3'-indolin]-6'-yl)-1-cyclohexene-1,2-dicarboximide | 0.500 0.250 0.125 | 2.0 0.0 0.0 | 0.0 0.0 0.0 | 4.0 2.0 1.0 | 5.0 6.0 7.0 | 9.0 9.0 9.0 | 7.0 6.0 6.0 | 9.0 9.0 6.0 | 5.0 4.0 4.0 | 2.0 1.0 0.0 | 0.0 0.0 0.0 | 0.0 0.0 0.0 |
| N-(1'-Acetyl-5'-fluoro-2'-oxospiro[cyclopropane-1,3'-indolin]-6'-yl)-1-cyclohexene-1,2-dicarboximide | 0.500 0.250 | 0.0 0.0 | 0.0 0.0 | 2.0 0.0 | 5.0 2.0 | 9.0 9.0 | 8.0 7.0 | 9.0 8.0 | 1.0 0.0 | 0.0 0.0 | 0.0 0.0 | 0.0 |
| 6'-(1-Cyclohexene-1,2-dicarboximido)-5'-fluoro-1'-(2-propynyl)spiro[cyclopropane-1,3'-indolin]-2'-one | 0.500 0.125 0.032 | 6.0 5.0 4.0 | 6.0 5.0 3.0 | 8.0 8.0 7.0 | 9.0 9.0 9.0 | 9.0 9.0 9.0 | 9.0 9.0 9.0 | 9.0 9.0 9.0 | 9.0 9.0 3.0 | 7.0 2.0 2.0 | 5.0 4.0 2.0 | — 2.0 1.0 |
| 6'-(1-Cyclohexene-1,2-dicarboximido)-5'-fluoro-1'-methyl)spiro[cyclopropane-1,3'-indolin]-2'-one | 0.500 0.125 0.032 | 2.0 1.0 0.5 | 2.0 1.0 0.0 | 4.0 2.5 1.5 | 8.0 7.5 7.0 | 9.0 8.5 8.5 | 7.5 7.0 5.0 | 9.0 9.0 8.5 | 4.5 4.0 1.5 | 3.5 3.0 1.5 | 1.5 1.0 0.0 | 1.0 0.0 0.0 |
| N-(1'-Acetyl-2'-oxospiro[cyclopropane-1,3'-indolin]-6'-yl)-1-cyclohexene-1,2-dicarboximide | 1.000 | 0.0 | 2.0 | 4.0 | 7.0 | — | 8.0 | 8.0 | — | — | — | — |
| N-(2'-Oxospiro[cyclopropane-1,3'-indolin]-6'-yl)-1-cyclohexene-1,2-dicarboximide | 0.500 0.250 | 0.0 0.0 | 0.0 0.0 | 0.0 0.0 | 1.0 0.0 | 3.0 0.0 | 0.0 0.0 | 0.0 0.0 | 1.0 0.0 | 0.0 0.0 | 0.0 0.0 | 0.0 0.0 |
| 6'-(1-Cyclohexene-1,2-dicarboximido)-1'-methyl)spiro[cyclopropane-1,3'-indolin]-2'-one | 0.500 0.250 | 2.0 1.0 | 1.0 1.0 | 1.0 1.0 | 7.0 5.0 | 9.0 9.0 | 4.0 4.0 | 9.0 6.0 | 1.0 1.0 | 4.0 2.0 | 0.0 0.0 | 0.0 0.0 |
| 6'-(1-Cyclohexene-1,2-dicarboximido)-1'-(2-propynyl)spiro[cyclopropane-1,3'-indolin]-2'-one | 0.500 0.125 0.032 | 1.0 0.0 1.0 | 2.0 1.0 1.0 | 1.0 0.0 0.0 | 9.0 9.0 9.0 | 9.0 9.0 9.0 | 9.0 8.0 7.0 | 9.0 9.0 9.0 | 2.0 0.0 1.0 | 6.0 5.0 5.0 | 2.0 2.0 1.0 | 2.0 1.0 0.0 |
| 6'-(1-Cyclohexene-1,2-dicarboximido)-1'-(2-propenyl)spiro[cyclopropane-1,3'-indolin]- | 0.500 0.125 | 2.0 1.0 | 2.0 1.0 | 2.0 0.0 | 9.0 6.0 | 9.0 9.0 | 8.0 6.0 | 9.0 8.0 | 2.0 2.0 | 4.0 3.0 | 2.0 1.0 | 0.0 0.0 |

TABLE I-continued

Postemergence Herbicidal Evaluation of Test Compounds

| Compound | Rate kg/ha | Barnyard Gr | large crab | Green Fox | Mrnglry Sp | Pigweed Sp | Rag weed | Velvet leaf | Corn Field | Soy bean | Rice Uplnd | W.Wheat at XX |
|---|---|---|---|---|---|---|---|---|---|---|---|---|
| 6'-(1-Cyclohexene-1,2 dicarboximido)-1'-(methoxymethyl)spiro[cyclopropane-1,3'-indolin]-2'-one | 0.500 0.125 | 2.0 1.0 | 2.0 1.0 | 2.0 0.0 | 9.0 7.0 | 9.0 9.0 | 7.0 7.0 | 9.0 9.0 | 1.0 1.0 | 5.0 5.0 | 2.0 1.0 | 2.0 0.0 |
| N-[5-Fluoro-3-(methyl-thio)-2-oxo-4-indolinyl]-1-cyclohexene-1,2-dicarboximide | 4.000 0.500 | 0.0 0.0 | 0.0 0.0 | 0.0 0.0 | 0.0 3.0 | — 3.0 | 0.0 1.0 | 0.0 0.0 | — 0.0 | — 0.0 | — 0.0 | — 0.0 |
| N-[5-Fluoro-3-methyl-3-(methylthio)-2-oxo-4-indolinyl]-1-cyclohexene-1,2-dicarboximide | 4.000 0.500 | 0.0 0.0 | 0.0 0.0 | 0.0 0.0 | 0.0 3.0 | — 3.0 | 0.0 1.0 | 0.0 9.0 | — 0.0 | — 6.0 | — 0.0 | — 0.0 |
| N-[(5-Fluoro-1,3-dimethyl-3-(methylthio)-2-oxo-4-indolinyl]-1-cyclohexene-1,2-dicarboximide | 4.000 0.500 | 0.0 0.0 | 0.0 0.0 | 0.0 0.0 | 0.0 0.0 | — 0.0 | 0.0 0.0 | 0.0 0.0 | — 0.0 | — 0.0 | — 0.0 | — 0.0 |
| N-[6-Fluoro-3-methyl-3-(methylthio)-2-oxo-5-indolinyl]-1-cyclohexene-1,2-dicarboximide | 0.500 | 0.0 | 0.0 | 0.0 | 2.0 | 0.0 | 0.0 | 2.0 | 3.0 | 0.0 | 0.0 | 0.0 |
| N-[6-Fluoro-1,3-dimethyl-3-(methylthio)-2-oxo-5-indolinyl]-1-cyclohexene-1,2-dicarboximide | 0.500 0.125 | 1.5 5.0 | 1.5 4.5 | 1.0 4.5 | 9.0 7.0 | 9.0 8.5 | 7.0 5.0 | 9.0 9.0 | 3.5 3.0 | 1.5 0.5 | 0.5 0.0 | 0.0 0.0 |
| N-(4-Fluoro-1,3-dimethyl-3-(methylthio)-2-oxo-5-indolinyl)-1-cyclohexene-1,2-dicarboximide | 4.000 0.500 | 2.0 0.0 | 2.0 0.0 | 4.0 0.0 | 2.0 2.0 | — 2.0 | 7.0 2.0 | 8.0 3.0 | — 2.0 | — 0.0 | — 0.0 | — 0.0 |

EXAMPLE 15

Preemergence herbicidal evaluation of test compounds

The preemergence herbicidal activity of the compounds of the invention is exemplified by the following tests in which the seeds of a variety of monocotyledenous and dicotyledenous plants are separately mixed with potting soil and planted on top of about one inch of soil in jiffy flats. After planting, the flats are sprayed with selected aqueous acetone solutions containing test compound in sufficient quantity to provide the equivalent of about 0.500 to 4.000 kg/ha of test compound per flat. The treated flats are then placed on greenhouse benches and cared for in accordance with conventional greenhouse procedures. From 2 to 3 weeks after treatment, the flats are examined and the plants are rated according to the rating system set forth above. The data obtained are shown in Table II.

TABLE II

Preemergence Herbicidal Evaluation of Test Compounds

| Compound | Rate kg/ha | Barnyard Gr | large crab | Green Fox | Mrnglry Sp | Pigweed Sp | Rag weed | Velvet leaf | Corn Field | Soy bean | Rice Uplnd | W.Wheat at XX |
|---|---|---|---|---|---|---|---|---|---|---|---|---|
| N-[5-Fluoro-3-(methylthio)-2-oxo-6-indolinyl]-1-cyclohexene-1,2-dicarboximide | 0.500 | 0.0 | 0.0 | 0.0 | 0.0 | 0.0 | 0.0 | 0.0 | 0.0 | 0.0 | 0.0 | 0.0 |
| N-[(5-Fluoro-3-methyl-3-(methylthio)-2-oxo-6-indolinyl]-1-cyclohexene-1,2-dicarboximide | 0.500 | 2.5 | 0.5 | 1.0 | 3.0 | 4.5 | 3.5 | 4.5 | 0.0 | 0.0 | 0.0 | 0.0 |
| N-(5'-Fluoro-2'-oxospiro[cyclopropane-1,3'-indolin]-6'-yl)-1-cyclohexene-1,2-dicarboximide | 0.500 | 5.0 | 5.0 | 5.0 | 3.0 | 9.0 | 6.0 | 9.0 | 0.0 | 0.0 | 0.0 | 0.0 |
| N-(1'-Acetyl-5'-fluoro-2'-oxospiro[cyclopropane-1,3'-indolin]-6'-yl)-1-cyclohexene-1,2-dicarboximide | 0.500 | 1.0 | 3.0 | 7.0 | 0.0 | 9.0 | 4.0 | 0.0 | 0.0 | 0.0 | 0.0 | 0.0 |
| 6'-(1-Cyclohexene-1,2-dicarboximido)-5'-fluoro-1'-(2-propynyl)spiro[cyclopropane-1,3'-indolin]-2'-one | 0.500 | 9.0 | 9.0 | 9.0 | 9.0 | 9.0 | 9.0 | 9.0 | 7.0 | 9.0 | 3.0 | 6.0 |
| 6'-(1-Cyclohexene-1,2-dicarboximido)-5'-fluoro-1'-methyl)spiro[cyclopropane-1,3'-indolin]-2'-one | 0.500 | 5.5 | 6.5 | 7.5 | 4.0 | 9.0 | 6.0 | 9.0 | 0.0 | 1.5 | 0.0 | 1.5 |
| N-(1'-Acetyl-2'-oxospiro[cyclopropane-1,3'-indolin]-6'-yl)-1-cyclohexene-1,2-dicarboximide | 1.000 | 0.0 | 1.0 | 1.5 | 0.0 | — | 1.5 | 1.5 | 0.0 | 0.0 | 0.0 | — |
| N-[2'-Oxospiro[cyclopropane-1,3'-indolin]-6'-yl)-1-cyclohexene-1,2-dicarboximide | 0.500 | 0.0 | 0.0 | 0.0 | 0.0 | 0.0 | 0.0 | 0.0 | 0.0 | 0.0 | 0.0 | 0.0 |
| 6'-(1-Cyclohexene-1,2-dicarboximido)-1'-methyl)spiro[cyclopropane-1,3'-indolin]-2'-one | 0.500 | 0.0 | 0.0 | 0.0 | 0.0 | 0.0 | 0.0 | 0.0 | 0.0 | 0.0 | 0.0 | 0.0 |
| 6'-(1-Cyclohexene-1,2-dicarboximido)-1'-(2-propynyl)spiro[cyclopropane-1,3'-indolin]-2'-one | 0.500 | 8.0 | 8.0 | 8.0 | 9.0 | 9.0 | 9.0 | 9.0 | 6.0 | 3.0 | 2.0 | 3.0 |
| 6'-(1-Cyclohexene-1,2-dicarboximido)-1'-(2-propenyl)spiro[cyclopropane-1,3'-indolin]-2'-one | 0.500 | 5.0 | 6.0 | 7.0 | 9.0 | 9.0 | 4.0 | 9.0 | 0.0 | 0.0 | 0.0 | 0.0 |

TABLE II-continued

Preemergence Herbicidal Evaluation of Test Compounds

| Compound | Rate kg/ha | Barnyard Gr | large crab | Green Fox | Mrnglry Sp | Pigweed Sp | Rag weed | Velvet leaf | Corn Field | Soy bean | Rice Uplnd | W.Wheat at XX |
|---|---|---|---|---|---|---|---|---|---|---|---|---|
| 6-(1-Cyclohexene-1,2 dicarboximido)-1'-(methoxymethyl)spiro-[cyclopropane-1,3'-indolin]-2'-one | 0.500 | 5.0 | 2.0 | 6.0 | 5.0 | 9.0 | 3.0 | 9.0 | 4.0 | 0.0 | 1.0 | 0.0 |
| N-[5-Fluoro-3-(methyl-thio)-2-oxo-4-indolinyl]-1-cyclohex=n-1,2-dicarboximide | 4.000 | 0.0 | 0.0 | 0.0 | 0.0 | — | 0.0 | 0.0 | — | — | — | — |
| N-[5-Fluoro-3-methyl-3-(methylthio)-2-oxo-4-indolinyl]-1-cyclohexene-1,2-dicarboximide | 4.000 | 0.0 | 0.0 | 0.0 | 0.0 | — | 0.0 | 0.0 | — | — | — | — |
| N-[(5-Fluoro-1,3-dimethyl-3-(methylthio)-2-oxo-4-indolinyl]-1-cyclohexene-1,2-dicarboximide | 4.000 | 0.0 | 0.0 | 0.0 | 0.0 | — | 0.0 | 0.0 | — | — | — | — |
| N-[6-Fluoro-3-methyl-3-(methylthio)-2-oxo-5-indolinyl]-1-cyclohexene-1,2-dicarboximide | 0.500 | 0.0 | 0.0 | 0.0 | 0.0 | 0.0 | 0.0 | 0.0 | 0.0 | 0.0 | 0.0 | 0.0 |
| N-[6-Fluoro-1,3-dimethyl-3-(methylthio)-2-oxo-5-indolinyl]-1-cyclohexene-1,2-dicarboximide | 0.500 | 2.0 | 3.5 | 1.0 | 0.0 | 9.0 | 0.0 | 4.5 | 0.0 | 1.0 | 0.0 | 1.5 |
| N-(4-Fluoro-1,3-dimethyl-3-(methylthio)-2-oxo-5-indolinyl)-1-cyclohexene-1,2-dicarboximide | 0.500 | 0.0 | 0.0 | 0.0 | 0.0 | 0.0 | 0.0 | 0.0 | 0.0 | 0.0 | 0.0 | 0.0 |

EXAMPLE 16

Preemergence Herbicidal Evaluation In The Presence of Transplanted Rice

The selectivity of the compounds of the invention is exemplified by the following tests in which 2 ten-day old rice seedlings are transplanted into a 32 oz plastic container with a diameter of 10.5 cm containing 700 g of a silt loam soil. Seeds or barnyardgrass, an important weed species in transplanted rice culture, are planted in the top 0.5-1.0 cm of soil. After planting, the containers are flooded and the water level is maintained at 0.5 to 3.0 cm above the soil surface. Three to seven days after transplanting, the flooded soil surface of the cups are treated with the selected aqueous acetone solution containing test compound in sufficient quantity to provide the equivalent of about 0.040 to 0.060 kg per hectare of test compound per cup. The treated cups are then placed on greenhouse benches, watered such that the water level is maintained as stated above and cared for in accordance with conventional greenhouse practice. Three to five weeks after treatment, the tests are terminated and each cup is examined and rated according to the rating system provided in Example 14. The data obtained are reported in Table III below.

| Column Heading | Plant Species Used | |
|---|---|---|
| | Common Name | Scientific Name |
| Barnydgr | Barnyardgrass | *Echinochloa crus-(L) beau* |
| Rice Tebon | Rice Cv. Tebonnet | *Oryza sativa* |

TABLE III

| Preemergence Herbicidal Evaluation In The Presence of Transplanted Rice | | | |
|---|---|---|---|
| Compound Name | Rate kg/ha | Rice Tebon | Barn ydgr |
| 6'-(1-cyclohexene-1,2-dicarboximido)-5'-fluoro-1'-2-propynyl)-spiro[cyclopropane-1,3'-indolin]-2'-one | 0.060 | 1.5 | 9 |
| | 0.050 | 1 | 9 |
| | 0.040 | 1 | 8 |

We claim:

1. A compound having the structure

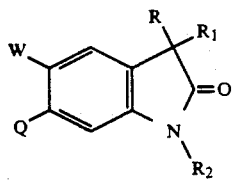

or

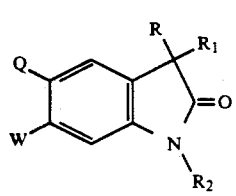

wherein r is hydrogen or $C_1$-$C_6$ alkyl optionally substituted with hydroxy, $C_1$-$C_4$ alkoxy, mercapto, $C_1$-$C_4$ alkylthio, amino, carboxy or carb($C_1$-$C_4$)alkyloxy;

$R_1$ is $C_1$-$C_6$alkylthio; and when R and $R_1$ are taken together with the carbon to which they are attached they represent saturated or unsaturated $C_3$-$C_7$ cycloalkyl;

$R_2$ is hydrogen;
$C_1$-$C_4$ alkyl optionally substituted with $C_1$-$C_4$ alkoxy, $C_1$-$C_4$ alkylthio, carboxy or carb($C_1$-$C_4$)alkyloxy,
$C_3$-$C_4$ cycloalkyl optionally substituted with $C_1$-$C_4$ alkoxy,
$C_1$-$C_4$ alkylthio, carboxy or carb($C_1$-$C_4$) alkyloxy,
$C_3$-$C_4$ alkenyl,
$C_3$-$C_4$ alkynyl, or
cyclopropylmethyl;

W is hydrogen, halogen;
$C_1$-$C_3$ alkoxy optionally substituted with one or more halogen atoms, or
$C_1$-$C_3$ alkyl optionally substituted with one or more halogen atoms;

Q is

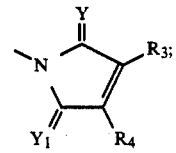

$R_3$ and $R_4$ are taken together with the atoms to which they are attached to form a four- to seven-membered saturated or unsaturated carbocyclic ring optionally substituted with one to three methyl groups or one or more halogen atoms; and Y and $Y_1$ are each independently O or S.

2. The compound according to claim 1 having the structure

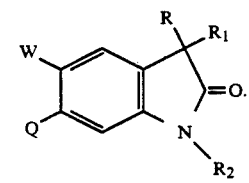

3. The compound according to claim 2 having the structure

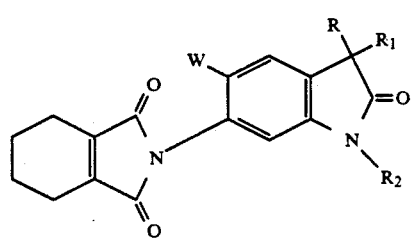

wherein
R is hydrogen or $C_1$-$C_4$ alkyl;
$R_1$ is $C_1$-$C_6$ alkylthio; and when R and $R_1$ are taken together with the carbon to which they are attached they represent $C_3$-$C_7$ cycloalkyl;

R₂ is $C_1$–$C_4$ alkyl optionally substituted with $C_1$–$C_4$ alkoxy or $C_1$–$C_4$ alkylthio,
$C_3$–$C_4$ cycloalkyl,
$C_3$–$C_4$ alkenyl,
$C_3$–$C_4$ alkynyl, or
cyclopropylmethyl; and
W is hydrogen or halogen.

4. The compound according to claim 3, 6'-(1-cyclohexene-1,2-dicarboximido)-5'-fluoro-1'-(2-propynyl)spiro[cyclopropane-1,3'-indolin]-2'-one.

5. The compound according to claim 3, N-{5'-fluoro-2'-oxospiro[cyclopropane-1,3'-indolin]-6'-yl}-1-cyclohexene-1,2-dicarboximide.

6. The compound according to claim 3, N-(1'-acetyl-5'-fluoro-2'-oxospiro[cyclopropane-1,3'-indolin]-6'-yl)-1-cyclohexene-1,2-dicarboximide.

7. The compound according to claim 3, 6'-(1-cyclohexene-1,2-dicarboximido)-5'-fluoro-1'-methyl)-spiro[cyclopropane-1,3'-indolin]-2'-one.

8. The compound according to claim 3, 6'-(1-cyclohexene-1,2-dicarboximido)-1'-(2-propynyl)-spiro[cyclopropane-1,3'-indolin]-2'-one.

9. The compound according to claim 3, N-{2'-oxospiro[cyclopropane-1,3'-indolin]-6'-yl}-1-cyclohexene-1,2-dicarboximide.

10. The compound according to claim 3, 6'-(1-cyclohexene-1,2-dicarboximido)-1'-(2-propenyl)-spiro[cyclopropane-1,3'-indolin]-2'-one.

11. A method for controlling undesirable plant species which comprise applying to the foliage of said plants or to the soil or water containing seeds or other propagating organs thereof, a herbicidally effective amount of a compound having the structure

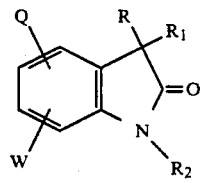

wherein R, $R_1$, $R_2$, Q and W are as described in claim 1.

12. The method according to claim 11 wherein the compound has the structure

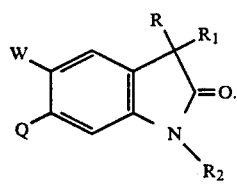

13. The method according to claim 12 wherein the compound has the structure

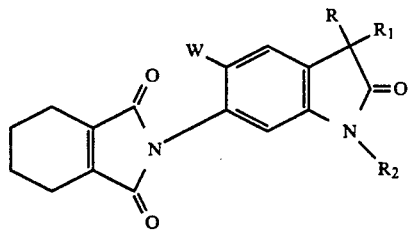

wherein
R is hydrogen or $C_1$–$C_4$ alkyl;
$R_1$ is $C_1$–$C_6$ alkylthio; and when R and
$R_1$ are taken together with the carbon to which they are attached they represent $C_3$–$C_7$ cycloalkyl;
R₂ is $C_1$–$C_4$ alkyl optionally substituted with $C_1$–$C_4$ alkoxy or $C_1$–$C_4$ alkylthio,
$C_3$–$C_4$ cycloalkyl,
$C_3$–$C_4$ alkenyl,
$C_3$–$C_4$ alkynyl, or
cyclopropylmethyl; and
W is hydrogen or halogen.

14. The method according to claim 13 wherein the compound is selected from the group consisting of 6'-(1-cyclohexene-1,2-dicarboximido)-5'-fluoro-1'-(2-propynyl)spiro[cyclopropane-1,3'-indolin]-2'-one; N-{5'-fluoro-2'-oxospiro[cyclopropane-1,3'-indolin]-6'-yl}-1-cyclohexene-1,2-dicarboximide; N-(1'-acetyl-5'-fluoro-2'-oxospiro[cyclopropane-1,3'-indolin]-6'-yl)-1-cyclohexene-1,2-dicarboximide; 6'-(1-cyclohexene-1,2-dicarboximido)-5'-fluoro-1'-methyl)-spiro[cyclopropane-1,3'-indolin]-2'-one; 6'-(1-cyclohexene-1,2-dicarboximido)-1'-(2-propynyl)-spiro[cyclopropane-1,3'-indolin]-2'-one; 6'-(1-cyclohexene-1,2-dicarboximido)-1'-(2-propenyl)-spiro[cyclopropane-1,3'-indolin]-2'-one; 6'-(1-cyclohexene-1,2-dicarboximido)-1'-methyl)spiro[cyclopropane-1,3'-indolin]-2'-one; and 6'-(1-cyclohexene-1,2-dicarboximido)-1'-(methoxymethyl)spiro[cyclopropane-1,3'-indolin]-2'-one.

15. The method according to claim 11 which comprises applying said compound to the foliage of said plants at a rate of about 0.016 kg/ha to 4.0 kg/ha.

16. The method according to claim 11 which comprises applying said compound to the soil or water containing seeds or other propagating organs of said plants at a rate of about 0.016 kg/ha to 4.0 kg/ha.

17. A composition for controlling undesirable plant species which comprises an agronomically acceptable carrier and a herbicidally effective amount of a compound as described in claim 1.

18. A method for the selective control of undesirable plant species in the presence of transplanted rice which comprises applying to the flood water or soil as a pre-emergence post-transplant treatment a herbicidally effective amount of a compound described in claim 1.

19. The method according to claim 18 wherein said compound is as described in claim 2.

20. The method according to claim 18 wherein the compound is applied to the flood water or soil at a rate of about 0.016 kg/ha to 4.0 kg/ha.

* * * * *